United States Patent
Liu et al.

(10) Patent No.: US 11,551,352 B2
(45) Date of Patent: Jan. 10, 2023

(54) SYSTEMS AND METHODS FOR X-RAY IMAGING

(71) Applicant: GE Precision Healthcare LLC, Milwaukee, WI (US)

(72) Inventors: Xiaosong Liu, Beijing (CN); Yanhua Shi, Beijing (CN)

(73) Assignee: GE Precision Healthcare LLC, Milwaukee, WI (US)

( * ) Notice: Subject to any disclaimer, the term of this patent is extended or adjusted under 35 U.S.C. 154(b) by 117 days.

(21) Appl. No.: 16/741,456

(22) Filed: Jan. 13, 2020

(65) Prior Publication Data

US 2021/0217163 A1    Jul. 15, 2021

(51) Int. Cl.
- *G06T 7/00* (2017.01)
- *G06T 5/00* (2006.01)
- *A61B 6/00* (2006.01)

(52) U.S. Cl.
CPC ............ *G06T 7/0012* (2013.01); *A61B 6/487* (2013.01); *A61B 6/52* (2013.01); *G06T 5/008* (2013.01); *G06T 2207/10121* (2013.01); *G06T 2207/30004* (2013.01)

(58) Field of Classification Search
CPC .................. G06T 7/0012; G06T 5/008; G06T 2207/30004; G06T 2207/10121; A61B 6/52; A61B 6/487

USPC ......................................................... 382/128
See application file for complete search history.

(56) References Cited

U.S. PATENT DOCUMENTS

| | | | |
|---|---|---|---|
| 2013/0077750 A1* | 3/2013 | Yabugami | A61B 6/481 378/62 |
| 2014/0253764 A1* | 9/2014 | Haas | G06T 5/008 348/243 |
| 2014/0376814 A1* | 12/2014 | Hirooka | G06T 5/008 382/195 |
| 2019/0246999 A1* | 8/2019 | Liu | A61B 6/5235 |
| 2020/0205767 A1* | 7/2020 | Niwa | A61B 6/487 |
| 2021/0093265 A1* | 4/2021 | Decker | A61B 6/4225 |
| 2021/0217163 A1* | 7/2021 | Liu | A61B 6/545 |

* cited by examiner

*Primary Examiner* — Amandeep Saini

(57) ABSTRACT

Methods and systems are provided for controlling an x-ray imaging system. In one embodiment, a method for an x-ray imaging system includes acquiring, with the x-ray imaging system, a first image as an x-ray tube current of the x-ray imaging system is ramping to a target x-ray tube current, determining a corrected brightness of the first image, the corrected brightness including a measured brightness of the first image corrected by a feedback x-ray tube current relative to the target x-ray tube current, and updating the target x-ray tube current based on the corrected brightness of the first image.

7 Claims, 4 Drawing Sheets

SYSTEMS AND METHODS FOR X-RAY IMAGING

FIELD

Embodiments of the subject matter disclosed herein relate to medical imaging, and more particularly, to x-ray fluoroscopic imaging.

BACKGROUND

Non-invasive imaging technologies allow images of the internal structures or features of a patient or object to be obtained without performing an invasive procedure on the patient or object. In particular, such non-invasive imaging technologies rely on various physical principles, such as the differential transmission of x-rays through the target volume or the reflection of acoustic waves, to acquire data and to construct images or otherwise represent the observed internal features of the patient or object.

For example, in fluoroscopy and other x-ray based imaging technologies, x-ray radiation is directed toward a subject, typically a patient in a medical diagnostic application, a package or baggage in a security screening application, or a fabricated component in an industrial quality control or inspection application. A portion of the radiation impacts a detector where the image data is collected and used in an image generation process. In the images produced by such systems, it may be possible to identify and examine the internal structures and organs within a patient's body, objects within a package or container, or defects (e.g., cracks) within a fabricated component. In certain contexts, such as fluoroscopy applications used in support of interventional or navigation procedures, low-dose x-rays may be acquired at a high frame rate over an extended period to provide real-time image data that may be used to guide or navigate a tool within a patient.

BRIEF DESCRIPTION

In one embodiment, a method for an x-ray imaging system includes acquiring, with the x-ray imaging system, a first image as an x-ray tube current of the x-ray imaging system is ramping to a target x-ray tube current, determining a corrected brightness of the first image, the corrected brightness including a measured brightness of the first image corrected by a feedback x-ray tube current relative to the target x-ray tube current, and updating the target x-ray tube current based on the corrected brightness of the first image.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
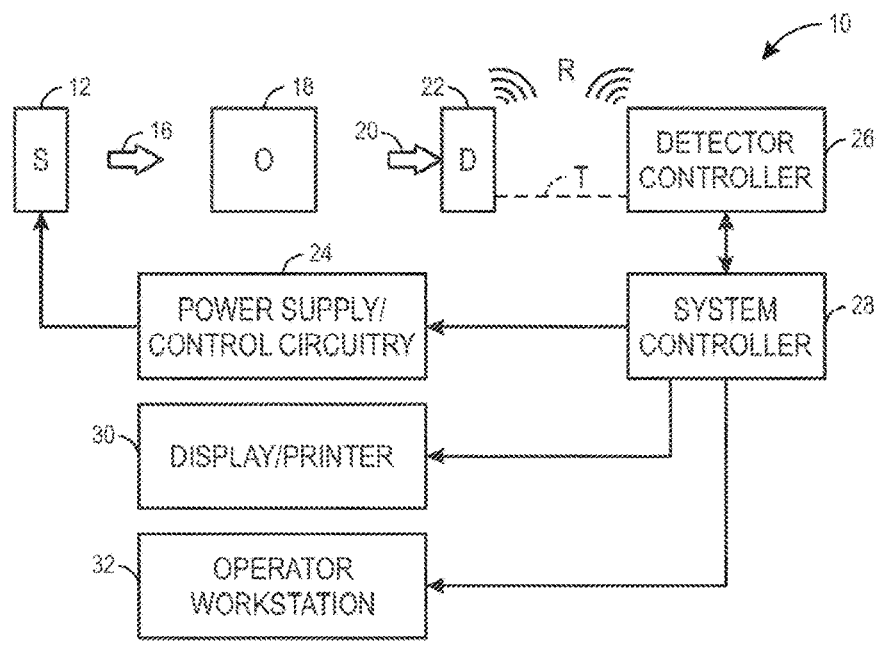
FIG. 1 depicts a block-diagram of an embodiment of a digital x-ray imaging system, in accordance with aspects of the present disclosure.

The following description relates to various embodiments of reducing the time from initiation of x-ray imaging until images having stabilized/target brightness are acquired. During a surgical procedure monitored/assisted by fluoroscopic imaging, continuous, real-time x-ray images of a patient may be displayed, allowing clinicians to monitor movement of anatomical features. During such procedures, it may also be useful to occasionally monitor the patient using single, still x-ray images. To initiate fluoroscopic imaging, an exposure control pedal may be depressed, e.g., by a foot of a clinician. A quick depression and release (e.g., tap) of the exposure control pedal may indicate the clinician is requesting a single x-ray image, where prolonged depression of the exposure control pedal may indicate the clinician is requesting fluoroscopic imaging.

Typically, to obtain a high-quality x-ray image, a sequence of steps are performed before a stabilized image is acquired and output for display, referred as auto brightness stabilization (ABS). These steps may include preparing the imaging system for exposure, exposing the patient to a beam of radiation by activating a radiation source (such as an x-ray tube), and adjusting the voltage and current of the radiation source based on the brightness of the resultant images acquired by the radiation detector. Once a target brightness has been reached, further image quality adjustments may be made by applying temporal noise filters, for example. Once the images reach a target contrast to noise ratio, a stabilized image may be acquired and output for display, which may then be followed by continuous imaging, if requested.

The ABS sequence described above may be relatively lengthy, in part because of a system delay owing to the time required to obtain an image frame, determine the brightness of the image frame, and then adjust the radiation source parameters based on the brightness of the image frame. Further, the radiation source is not able to rapidly reach a commanded current with certain types of x-ray tubes. Rather, while an x-ray tube may reach a commanded voltage nearly instantaneously, the current of the x-ray tube is based on the tube voltage and a temperature of the filament of the x-ray tube. Accordingly, the x-ray tube will not reach a commanded current until the filament is heated or cooled to a certain temperature, and the time it takes to change the filament temperature may be relatively long. During the time that the current is ramping toward the commanded current, images acquired may be saturated or otherwise too dark to sufficiently visualize anatomical features of the patient. Thus, the ABS sequence may wait until a target x-ray tube current is reached (e.g., 3.9 mA) and then images may be acquired. Once the images are acquired, the initial commanded voltage and current are further adjusted (e.g., based on the image brightness described above), as the actual tube voltage and current needed to acquire a high-quality image varies with patient anatomy, which also lengthens the process.

According to embodiments disclosed herein, the auto brightness stabilization sequence for a fluoroscopic imaging system may be shortened by utilizing a predicted brightness of the final, stabilized images, as input to determine the target x-ray imaging parameters (e.g., current, voltage, and camera gain) while the current is ramping toward a target current, based on the understanding that the brightness of an image is proportional to the current used to acquire that image. For example, the x-ray system may be activated with initial/default settings (e.g., voltage, current, and gain) and once a first image is obtained, the predicted brightness may be determined according to the relationship between the brightness of the first image and the x-ray tube current used to acquire the first image, rather than the actual brightness of the first image. This predicted brightness may be used to obtain a target voltage, current, and gain from a set of indexes, and the system is commanded to transmit a radiation beam at the target voltage and current. If the corrected brightness is not within a stable window surrounding a target brightness, this process may continue as the tube current is ramping from the initial current to the new target current until the stabilized images are achieved.

In this way, by using a predicted brightness of a future, stabilized image rather than current brightness of a current image, the time to actually reach the stabilized brightness may be decreased. In doing so, the amount of radiation the patient is exposed to may be lowered, and the stabilized images may be displayed more quickly than during the lengthier sequence described above, which may be beneficial during time-sensitive procedures. The image stabilization process described herein takes into account the actual x-ray tube current used to acquire an image. For example, the image may be acquired with a preset x-ray technique of 70 kV and 4 mA, but because of the slow response of the x-ray tube filament, the actual current at which the image is acquired may be 2 mA. The brightness of the image may be determined (e.g., a video level indicator (VLI) of 78). Without applying the brightness correction described herein, the kV/mA may be adjusted until the measured brightness is within a stable window (e.g., a VLI of ±6% of 110), which may take an unduly long amount of time as the system would need to wait until the current is stabilized to get a stabilized brightness to check. For example, a prior approach to acquiring images having a stabilized, target brightness includes waiting until brightness is stabilized, and then determining if the stabilized brightness if within a stable window, and if not, adjusting kV/mA. A further prior approach includes adjusting kV/mA for each frame in a small, step-wise manner regardless of whether brightness is stabilized. In either approach, the time to reach a target, stabilized brightness is slow.

In contrast, the stabilization process described herein may correct the brightness based on the actual x-ray tube current that the image was acquired at (as will be described in more detail below). In the example presented above where the measured brightness of the image is a VLI of 78 and the actual x-ray tube current is 2 mA, the corrected VLI may be 110, which is within the stable window, and thus the image would be determined to be stable and no additional adjustments to the voltage or current would be made. While the filament may take approximately 500 ms to fully reach a stable target current, the filament may reach 90% of the target current in approximately 200 ms, and thus after 200 ms, the brightness of the image may be robust enough to measure and, once corrected, predict that the stabilized brightness will be reached without further correcting the voltage or current. In doing so, the number of images that may be need to be obtained to check the brightness, and hence the number of adjustments made to the x-ray technique to reach the final, stabilized brightness, may be reduced.

Though a fluoroscopic imaging system is described by way of example, it should be understood that the present techniques may also be useful when applied to images acquired using other imaging modalities, such as standard, non-fluoroscopic x-ray imaging, tomosynthesis, and so forth. The present discussion of a fluoroscopic imaging modality is provided merely as an example of one suitable imaging modality.

FIG. 1 illustrates diagrammatically an imaging system 10 for acquiring and processing image data. In the illustrated embodiment, system 10 is a digital x-ray system designed both to acquire original image data and to process the image data for display. The imaging system 10 may be a stationary or mobile x-ray system. In the embodiment illustrated in FIG. 1, imaging system 10 includes a source of x-ray radiation 12 that emits a beam or stream of radiation 16 into a region in which an object or subject 18 is positioned. The x-ray radiation source 12 (which may comprise an x-ray generator and x-ray tube) is controlled by a power supply/control circuit 24 which furnishes both power and control signals for examination sequences. A portion of the radiation 20 passes through or around the subject and impacts a digital x-ray detector, represented generally at reference numeral 22. The detector 22 may be portable or permanently mounted to the system 10. In certain embodiments, the detector 22 may convert the incident x-ray photons to lower energy photons which are detected. Electrical signals are generated in response to the detected photons and these signals are processed to reconstruct an image of the features within the object or subject.

The detector array 22 may include one or more CMOS light imager panels, each separately defining an array of detector elements (e.g., pixels). Each detector element produces an electrical signal that represents the intensity of the x-ray beam incident at the position of the detector element when the beam strikes the detector 22. This signal may be digitized and sent to a monitor/display device for display. In the depicted example, the detector 22 includes or communicates with a detector controller 26 (e.g., control circuitry) which commands acquisition of the signals generated in the detector 22. In the presently illustrated embodiment, the detector 22 may communicate with the detector controller 26 via any suitable wireless communication standard (R), although the use of digital x-ray detectors 22 that communicate with the detector controller 26 through a cable (T) or some other mechanical connection are also envisaged. Alternatively, operational aspects of the detector controller 26 may be implemented on, or otherwise provided of, the detector 22 itself in some implementations. Detector controller 26 may also execute various signal processing and filtration functions, such as for initial adjustment of dynamic ranges, interleaving of digital image data, and so forth.

Both power supply/control circuit 24 and detector controller 26 are responsive to signals from a system controller 28. In general, system controller 28 commands operation of the imaging system to execute examination protocols and to process acquired image data. In the present context, system controller 28 may also include signal processing circuitry and one or more data storage structures, such as optical memory devices, magnetic memory devices, or solid-state memory devices, for storing programs and routines executed by a processor of the system 10 to carry out various functionalities, as well as for storing configuration parameters and image data. In one embodiment, a programmed computer system may be provided with hardware, circuitry, firmware, and/or software for performing the functions attributed to one or more of the power supply/control circuit 24, the detector controller 26, and/or the system controller 28.

In the embodiment illustrated in FIG. 1, system controller 28 is linked to at least one output device, such as a display or printer as indicated at reference numeral 30. The output device may include standard or special purpose monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, cloud-based network, and so forth.

The x-ray system 10 as shown in FIG. 1 may also include a variety of alternative embodiments generally configured to meet the particular needs of certain applications. For example, the x-ray system 10 may be either fixed, a mobile system, or a mobile C-arm system where the x-ray detector is either permanently mounted inside one end of the C-arm or removable from the system. Further, the x-ray system 10 may be a table and/or wall stand system in a fixed x-ray room where the x-ray detector 22 is either permanently mounted together with the system or portable. Alternatively, the x-ray system 10 may be a mobile x-ray system with a portable x-ray detector. Such a portable x-ray may be further constructed with a detachable tether or cable used to connect the detector readout electronics to the data acquisition system of the scanner. When not in use, a portable x-ray detector may be detached from the scan station for storage or transfer. In practice, the imaging system 10 may be any suitable x-ray based imaging system, including, but not limited to, conventional radiography systems, CT imaging systems, tomosynthesis systems, C-arm systems, fluoroscopy systems, mammography systems, dual- or multiple-energy systems, navigational or interventional imaging systems, and so forth. Further still, while an example of a flat-panel detector was described above, a digital detector system including image intensifier and video camera may be used to convert the incident x-rays to a video signal.

Figure 2:
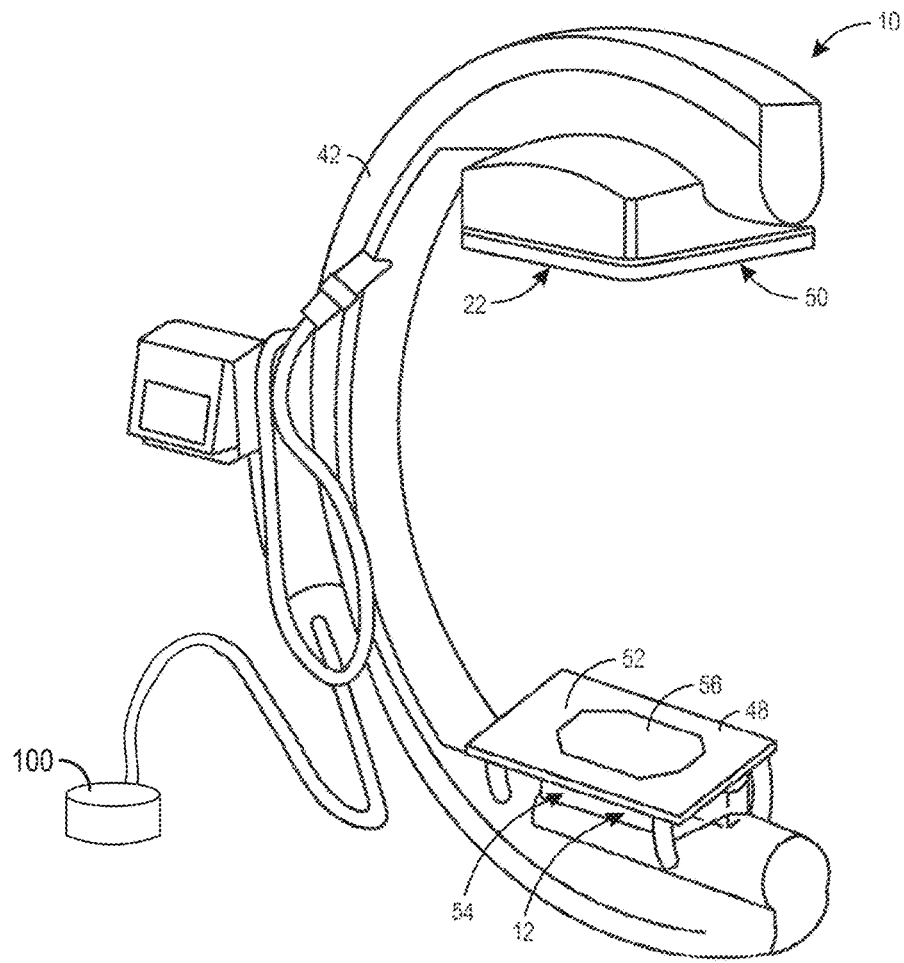
FIG. 2 depicts an implementation of an x-ray imaging system, in accordance with aspects of the present disclosure.

While the preceding schematically describes components of an x-ray based imaging system 10, including a detector and detector control and readout circuitry as discussed herein, FIG. 2 depicts an example of how such an imaging system 10 may be provided in a real-world context. As noted above, the x-ray system 10 may be implemented as a mobile x-ray device (e.g., an x-ray device comprising a C-arm, a mini C-arm, an O-arm, a non-circular arm, and so forth), and a fixed x-ray device. By way of illustration, FIG. 2 shows an x-ray imaging system 10 that comprises a C-arm x-ray device 42 configured to rotate a detector panel 22 and x-ray source 12 about a volume to be imaged. In the depicted example, the x-ray system 10 also includes a collimator 48. Any suitable x-ray source 12 can be used, including a standard x-ray source, a rotating anode x-ray source, a stationary or fixed anode x-ray source, a solid state x-ray emission source, or a fluoroscopic x-ray source 54 (as shown in FIG. 2). Any suitable x-ray detector 22 can be used, including a digital flat panel detector, an image intensifier, etc.

FIG. 2 shows an implementation in which the collimator 48 comprises an x-ray attenuating material 52 that defines an aperture 56 through which x-ray may pass, and which in turn prevents or limits x-ray emission beyond the bound of the defined aperture, thus shaping and limiting the defined beam. The collimator 48 can comprise any suitable x-ray attenuating material 52 that allows it to collimate an x-ray beam in this manner Some examples of suitable x-ray attenuating materials include tungsten, lead, gold, copper, tungsten-impregnated substrates (e.g., glass or a polymer impregnated with tungsten), coated substrates (e.g., glass or a polymer coated with tungsten, lead, gold, etc.), steel, aluminum, bronze, brass, rare earth metals, or combinations thereof.

Input to system controller 28 may be provided via one or more user input devices. FIG. 2 shows an example user input device in the form of a foot-pedal exposure pedal 100. Exposure pedal 100 may be connected via a suitable connection (e.g., wired or wireless) to system controller 28. Exposure pedal 100 may have a button that when depressed, signals to system controller 28 to initiate x-ray imaging. In one example, when exposure pedal 100 is depressed, a fluoroscopic imaging procedure is initiated. The fluoroscopic imaging procedure may include transmitting a beam of radiation toward a patient (e.g., via activation of x-ray source 12), where the portion of radiation that passes through or around the patient impinges on detector 22. Signals from detector 22 are then used to generate images for display. Once imaging parameters are adjusted so that the images reach a suitable level of quality (e.g., a target contrast to noise ratio), fluoroscopic imaging may commence (e.g., where the acquired images are displayed at a suitable frame rate, such as 30 fps). If the exposure pedal is released before the fluoroscopic imaging commences (e.g., during the series of steps where the imaging parameters are being adjusted to reach the target contrast to noise ratio), a toe-tap image may be displayed instead. The toe-tap image may be a single, non-moving x-ray image.

In order to acquire x-ray images of a specified brightness, the x-ray imaging system may be controlled according to an ABS routine that is executed by an ABS servo on the system controller (e.g., system controller 28). For example, depending on the type of imaging procedure, anatomy being imaged, etc., the x-ray imaging system may be controlled or commanded to output images having a specific brightness. Because of variation in patient size, anatomy density, etc., the x-ray imaging parameters (such as x-ray source voltage, x-ray source current, and camera/display/image gain) that will achieve the specific brightness are not known. The ABS routine may be executed to rapidly adjust the x-ray imaging parameters in order to output images having the specific brightness as quickly as possible. The ABS servo may include a set of index tables that may link specific current, voltage, and gain values. For example, the index tables may include a respective index table for each of current, voltage, and gain, with each imaging setting being plotted as a function of an index number ranging from 0 to 250, for example. An index may be selected based on a current image brightness relative to the target brightness. For example, if a current image has a brightness (defined by a video level indicator) of 50 and the target brightness is 110, a brightness variation of −60 may be determined by subtracting the target brightness from the current brightness (e.g., by subtracting 110 from 50).

This brightness variation may be entered into a look-up table that outputs an index skip, which defines how much the index should be changed. For example, if an image is obtained at default system parameters of 70 kV and 3.9 mA, the index at which the image was acquired may be 188. The look-up table may dictate an index skip of 62, based on a brightness variation of −60. Thus, the index may be changed from 188 to 250. The updated current, voltage, and gain values may be determined by obtaining the corresponding values from the index tables (e.g., the current, voltage, and gain values each corresponding to an index value of 250 may be obtained from the respective index tables), and the system may be commanded to operate at each of these parameters, and the process may repeat until the target brightness is reached.

As will be described in more detail below, this ABS routine may be shortened by determining a predicted brightness of one or more images acquired before the x-ray tube has reached a predefined, target current, rather than relying on the actual brightness of the images acquired once the predefined target current has been reached. The predicted brightness is determined based on the brightness of a current image and a ratio of the target current to a feedback current (which may be the current used to acquire the current image). By doing so, the ABS servo may determine how "far" from the target brightness the most recently acquired image is at, based on the ratio of the currents, and adjust the brightness that is entered into the look-up table accordingly. In this way, the auto stabilization of the brightness of the images may be performed while the x-ray tube is ramping toward the target current, which may decrease the time to reach the target brightness.

Figure 3:
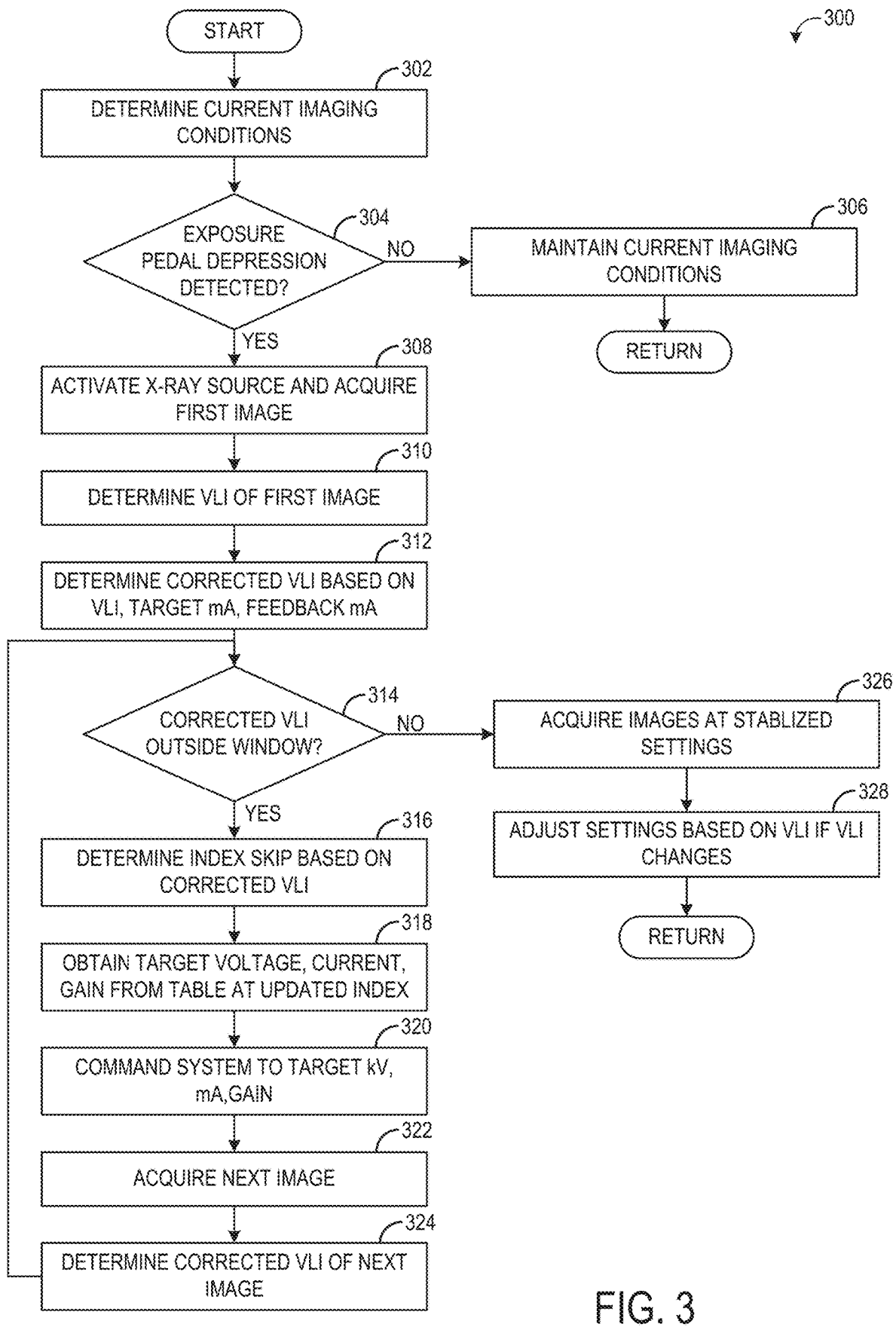
FIG. 3 is a flow chart illustrating a method for operating an x-ray imaging system.

Turning to FIG. 3, a method 300 for operating an x-ray imaging system, such as system 10 of FIGS. 1-2, is provided. The method will be described with regard to the systems and components described herein with regard to FIGS. 1-2, however it should be understood that the method may be implemented with other systems and components without departing from the scope of the present disclosure. Method 300 may be implemented as executable instructions in non-transitory memory of a computing device, such as system controller 28.

At 302, method 300 includes determining current imaging conditions. The determined current imaging conditions may include determining if x-ray imaging is currently occurring, the status of the exposure pedal (e.g., depressed or released), type of procedure being performed (such as vascular, cardiology, or spinal procedure), and/or other parameters. At 304, method 300 includes determining if an exposure pedal depression has been detected. As explained above, an x-ray imaging system, such as system 10, may include one or more user input devices, including an exposure pedal, such as exposure pedal 100. The exposure pedal may include a pedal/button that a clinician, such as a surgeon, may press to initiate x-ray imaging. To facilitate acquisition of x-ray images during surgical procedures, the exposure pedal may be a foot pedal configured to be depressed by a foot of the clinician, which may enable fluoroscopic imaging to be controlled in a hands-free manner, without disrupting clinical workflow. Thus, determining if a depression of the exposure pedal is detected may include receiving a user input signal from the exposure pedal commanding x-ray imaging to commence. The user input signal may be received continuously or periodically while the exposure pedal is depressed. In other examples, rather an exposure pedal being depressed, the user input signal may be received from another suitable input device, such as a keyboard, touchscreen, voice command, etc.

If depression of the exposure pedal is not detected, method 300 proceeds to 306 to maintain current imaging conditions. The current imaging conditions may include maintaining the radiation source of the x-ray imaging source deactivated (e.g., with no power supplied to the x-ray generator). In other examples, maintaining the current imaging parameters may include maintaining a current fluoroscopic imaging session. The detection of the depression of the exposure pedal may include detection of the exposure pedal going from released (e.g., not pressed) to being depressed. Thus, in examples where the exposure pedal is already pressed when method 300 executes, the current fluoroscopic imaging session may continue without disruption.

If depression of the exposure pedal is detected, method 300 proceeds to 308 to activate the x-ray source and acquire a first image. For example, upon detecting the depression of the exposure pedal, the x-ray imaging system may prepare for exposure of radiation, for example by commanding the x-ray generator and x-ray tube to prepare generating x-rays with a predetermined tube voltage (e.g., peak voltage kVp, which is the maximal voltage across the x-ray tube), a predetermined tube current (e.g., the number of electrons that jump from the cathode to the anode of the tube, represented in mA), and a predetermined pulse width. The system may also command the x-ray detector to prepare receiving x-rays with the commanded predetermined kVp, mA, and pulse width, at a predetermined frame rate, etc., and may also command the image processing unit to terminate any current tasks and prepare processing the incoming images. In one example, the predetermined kVp and the predetermined mA may be default system settings, such as 70 kV and 3.9 mA, but other predetermined voltages and currents are within the scope of this disclosure. In some examples, the predetermined kVp and mA may be based on a target brightness, which may be fixed or may vary based on the type of imaging being conducted, target anatomy being imaged, etc. For example, the target brightness may include a VLI of 110, and the predetermined kVp and mA may be the kVp and mA that would result in a VLI of 110 for a standard/average patient (e.g., as determined from a polymethylmethacrylate (PMMA) phantom).

In some examples, upon receiving a command to prepare for imaging, the x-ray detector may initiate scrubbing of the detector panel at a requested frame rate. The detector may then generate a synchronization signal when an equilibrium condition is reached and send the synchronization signal back to the system controller. The x-ray generator and x-ray tube may wait for the synchronization signal from the detector and start generating x-rays at the synchronization signal once x-ray exposure is enabled. The workstation/image processing unit may stop current activities, initialize the acquisition and image processing modules, and wait for incoming frames. Further, in some examples, during the exposure preparation phase, the filament of the x-ray tube may be pre-heated (e.g., via applying a certain amount of voltage over the filament prior to x-ray exposure) in order to reduce the amount of time for the x-ray tube to reach the commanded predefined current. For example, the filament may be heated to a predetermined temperature that is based on the predefined tube current such that the predefined tube current may be rapidly reached once exposure begins.

Once the system has commanded the components to prepare for generating/receiving x-rays, the system advances to a subsequent phase in the x-ray imaging sequence once all the components are ready (e.g., once the detector starts sending the synchronization signal, the x-ray generator sets a generator ready flag, and the workstation sets a workstation ready flag). The subsequent phase includes initiating x-ray exposure, where the x-ray tube is operated at the predefined kVp and mA. This causes x-rays to be generated and sent to, through, and around the patient, where the x-rays impinge on the detector, and the first image is acquired. The tube voltage may be reached relatively quickly, such as within 3 msec. However, because the tube current depends on tube filament temperature in addition to tube voltage, the target tube current may take a relatively long time to be reached, such as 300 msec or more. The first image may be acquired relatively quickly (e.g., 10 msec) after the exposure command is sent out. In some examples, the filament of the x-ray tube may be maintained at an elevated temperature (e.g., relative to room temperature) as explained above, which may allow the predefined current to be rapidly reached. For example, upon the exposure command being sent, it may take 7-8 msec for the x-ray tube current to reach 90% of the predefined/set tube current.

At 310, a video level indicator (VLI) of the first image is determined. The video level indicator may be a measurement of image brightness, and may include an average brightness of the image in a region of interest, such as a region of the image that corresponds to a center of the detector. At 312, a corrected VLI is determined based on the VLI of the first image, a target current, and a feedback current. The target current may be the predefined current discussed above (e.g., 3.9 mA), which may be the default current that the x-ray system is commanded to operate at until an updated target current is determined (explained in more detail below). The feedback current may be the x-ray tube current at the time the first image was acquired. The corrected VLI may be a prediction of the brightness of the image at the target current, taking into consideration the slow filament response. The brightness of an x-ray image is proportional to the x-ray tube current at which the image was acquired. When an image (such as the first image) is acquired while the current is ramping to the target current, the brightness of the image may be defined by:

$$\text{Bright} = \text{bright\_with\_unit}\_ma * ma_f \quad \text{(Eq. 1)}$$

In the above equation, $ma_f$ is the average (feedback) current of the x-ray source while the image was acquired and bright_with_unit$_{ma}$ is a conversation factor that relates units of current (mA) to brightness units (e.g., VLI) for a known imaging subject (e.g., a phantom). As such, eq. 1 demonstrates that the brightness of an image is proportional to the current at which that image was acquired. In an ideal system where the current responds immediately to a set value $ma_s$ (e.g., where the current immediately changes upon a command to change the current), the brightness should be:

$$\text{Bright}' = \text{Bright} * ma_s / ma_f \quad \text{(Eq. 2)}$$

In the above equation, Bright is the brightness acquired in the real system with a current ramping delay. This suggests that if a correction of Bright*$ma_s/ma_f$ is applied on real brightness, the system with the current ramping delay will be "changed" to an ideal system. Therefore, the restraint of a slow current response would not be a consideration if a correction is carried on real brightness, meanwhile the image brightness prediction and ABS stabilization prediction would also be realized.

Thus, the actual/applied current is monitored and recorded as the feedback current ($ma_f$) for each image frame in real time during the stabilization process. This feedback current is used to correct the VLI, as the VLI is proportional to the square root of brightness. For example, the corrected VLI (referred as vli') may be determined based on the measured VLI, feedback current, and target current, according to:

$$\text{vli}' = \text{vli} * \sqrt{ma_s/ma_f} \quad \text{(Eq. 3)}$$

In this way, the corrected VLI may be corrected by the feedback current in proportion to the set current (e.g., the target current). This corrected brightness may be used as the input to the ABS system rather than current brightness to adjust the x-ray parameters in order to reach a target brightness.

At 312, method 300 determines if the corrected VLI is outside a stable VLI window. The stable VLI window may include a threshold range around the target VLI, such as within 1-1.5% of the target VLI. Further, in order to be considered within the stable VLI window, the corrected VLI may be within the threshold of the target VLI for a given number of consecutive image frames, such as two or three.

If the corrected VLI is outside the stable VLI window, method 300 proceeds to 316 to determine an index skip based on the corrected VLI. To determine the index skip, a difference between the target VLI and the corrected VLI (referred as a VLI variation) is calculated and entered into an index skip look-up table, which outputs an index skip (also referred to as an index change) based on the VLI variation. The index is then changed based on the index skip, for example, according to:

$$f(n) = f(n-1) + \text{LUT}(\text{vli}_n) \quad \text{(Eq. 4)}$$

In the above equation, f(n−1) is the index of the most recently acquired image (e.g., the index that corresponds to the imaging parameters applied to acquire the image) and LUT (vli$_n$) is the index change as determined from the look-up table based on the corrected VLI.

Figure 4:
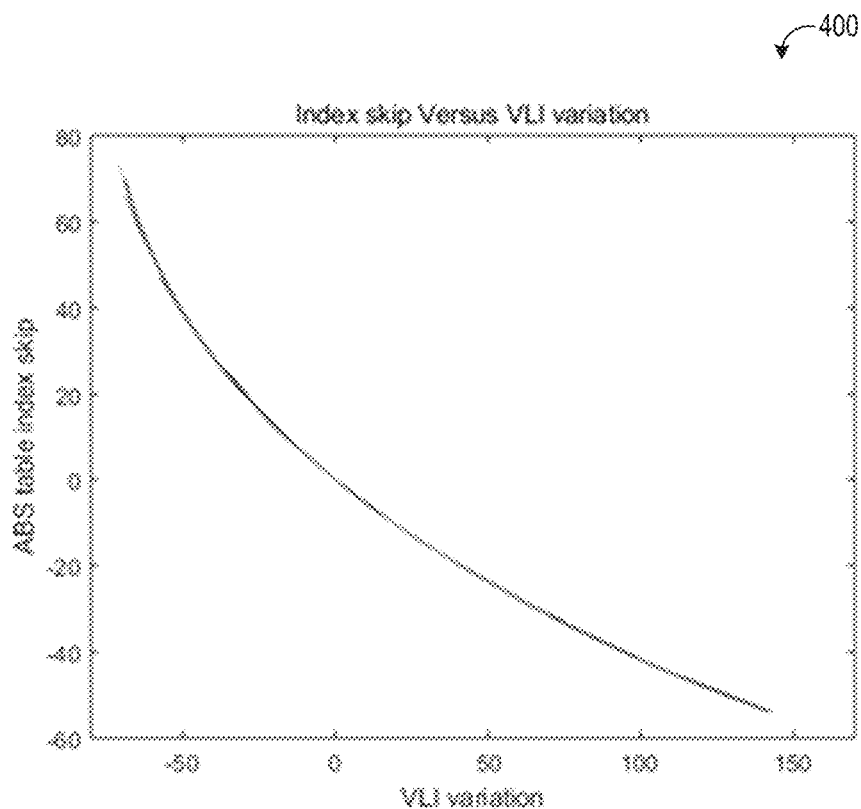
FIG. 4 shows an example index skip look-up table.

FIG. 4 shows an example index skip look-up table 400. The table 400 includes index skip plotted as a function of VLI variation. Because VLI and the index tables are both limited in their possible values (e.g., 0-255) and further because the VLI variation is relative to a target VLI that may be an intermediate value (e.g., 110), the table 400 only includes a limited set of index skip values (e.g., −60 to 80) and VLI variation values (e.g., −100 to 150), but other values are possible without departing from the scope of this disclosure. The relationship between the index skip and the VLI variation may be roughly exponential (with a negative decay), but other relationships are possible.

As an example, the voltage, current, and gain applied to acquire the first image may be determined and the index may be determined based on this voltage, current, and gain. The corrected VLI may be determined as described above, and the VLI variation may be determined by subtracting a target VLI (which may be a fixed value or may be determined based on a selected imaging protocol, imaged anatomy, user preferences, etc.) from the corrected VLI, e.g., VLI'−target VLI. If the corrected VLI is 90 and the target VLI is 110, the VLI variation may be −20, which may result in an index skip of 15. The index skip may be added to the index, causing an increase in the index. The updated index may then be used to obtain an updated target voltage, current, and gain, and the x-ray system may be commanded to operate at the updated target voltage, current, and gain.

Figure 5:
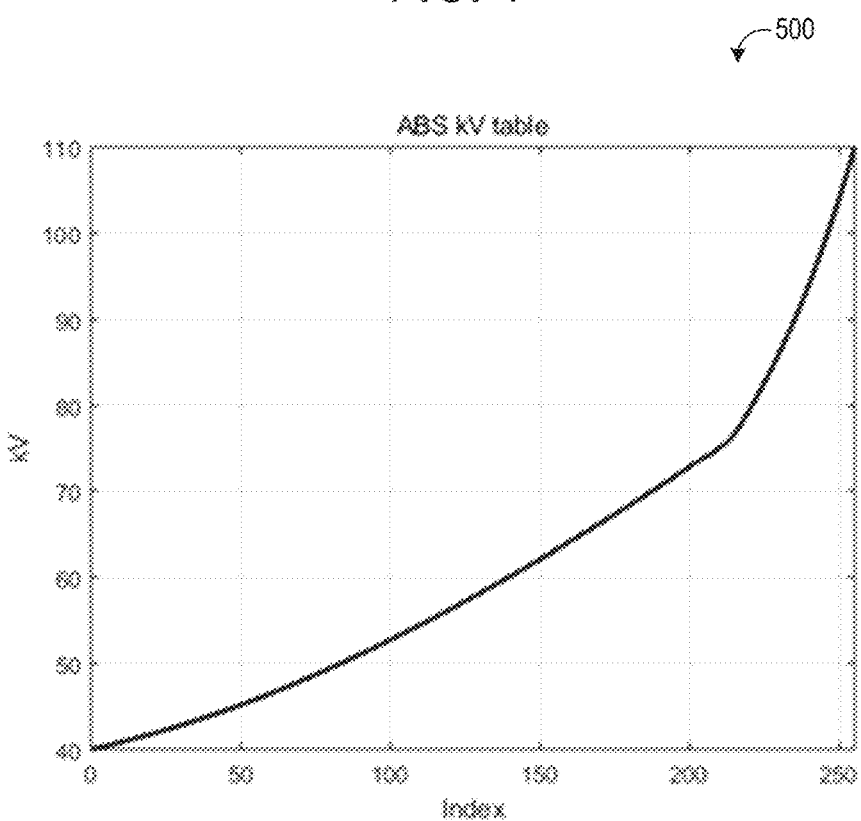
FIG. 5 shows an example index table.

Thus, at 318, an updated target voltage, current, and gain are determined from the index tables based on the updated index. FIG. 5 shows an example index table 500 for voltage. The index table 500 includes voltage (in kV) plotted as a function of index, which includes values ranging from 0-255. If the prior index (e.g., at which the first image was obtained) was 135 and the updated index is 150, for example, the prior target voltage may be 58 kV and updated target voltage may be 62 kV. A similar index table may be included for current and gain, and the updated index is used to determine each of the updated target current and gain.

At 320, the x-ray system is commanded to operate at the updated target voltage, the updated target current, and the updated target gain. At 322, a next image is acquired. At 324, the corrected VLI of the next image is determined, as explained above at 312 (e.g., the VLI of the next image is determined, the feedback current at which the next image was acquired is determined, and the corrected VLI is determined based on the VLI of the next image, the feedback current, and the target current, where the target current is the updated target current determined at 318). Method 300 then loops back to 314 to determine if the corrected VLI is outside the stable VLI window. If yes, the process repeats (an index skip is determined based on the corrected VLI of the next image, an updated target voltage, current, and gain are determined based on the index skip, the x-ray imaging system is commanded to operate at the updated settings, and a further next image is acquired).

If the corrected VLI is not outside the stable VLI window, method 300 proceeds to 326 to acquire one or more images at the stabilized settings (e.g., the current voltage, current, and gain). Images may be acquired and displayed at a suitable frame rate (e.g., 10-30 fps) until the exposure pedal is released or until another suitable signal is received commanding the imaging be terminated. If the exposure pedal has been released, radiation exposure may be terminated by terminating the power supply to the x-ray generator, thereby causing the tube voltage and current to drop to zero and the tube to stop generating x-rays.

During imaging, the patient may move, a needle or other device may be brought into the imaging field of view, and/or the position of the x-ray system may change (when mobile), each of which may cause a change in the brightness of the output images. Thus, in some examples, the imaging settings may be adjusted based on the VLI if the VLI changes, as indicated at 328. For example, the ABS servo may continue to determine the VLI, and if the VLI moves outside the stable window, the settings may be adjusted by entering the VLI variation into the index table look-up table and adjusting the index and hence the imaging settings, until the VLI returns to the stable window. Method 300 then returns.

Figure 6:
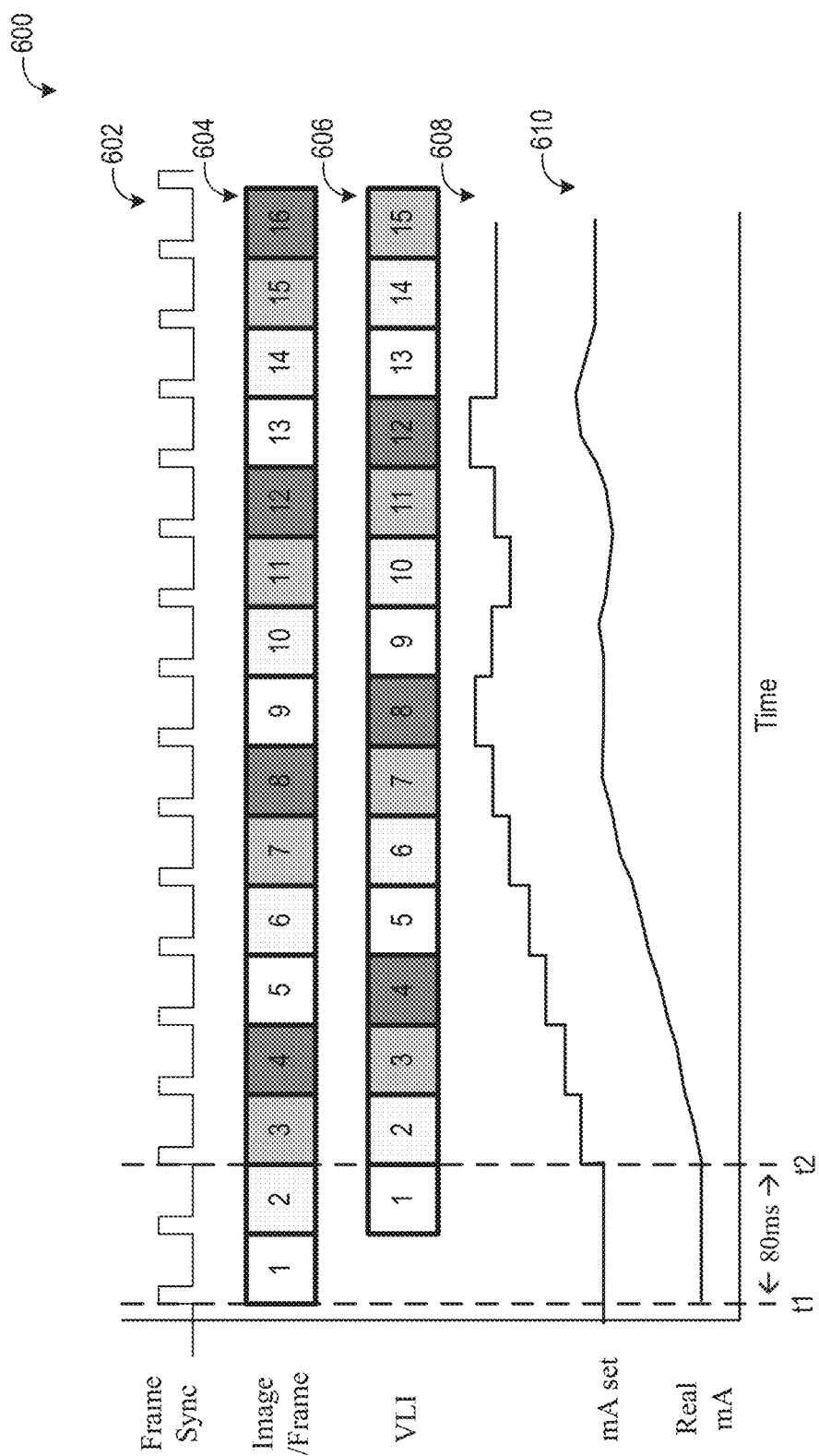
FIG. 6 shows an example timeline of image acquisition events, set current, and measured current during an auto brightness stabilization routine.

FIG. 6 illustrates a timeline 600 for a fluoroscopic imaging process that uses measured VLI to adjust imaging settings. Timeline 600 includes a first plot 602 illustrating the frame acquisition signal (frame sync) which indicates when each image frame is acquired, a second plot 604 illustrating the actual acquired frames, a third plot 606 of video level indicator for each frame, a fourth plot 608 of target x-ray source current (mA), and a fifth plot 610 of actual mA. For the plots illustrating mA, respective mA is depicted along the vertical axis, increasing from a lower value (e.g., 0) to a higher value (e.g., 5). All plots are illustrated as a function of time, and all plots are time-aligned. The third plot 606 showing VLI does not represent actual measured or corrected VLI but is merely intended to show when the VLI of a corresponding image is determined.

Prior to time t1, an operator (e.g., surgeon) depresses the exposure pedal and the tube voltage and current are both commanded to predefined values in order to begin transmitting an x-ray beam to a patient. At time t1, a first image is acquired. Once the first image is acquired, the VLI of the first image is determined. Once the VLI of the first image is determined, the VLI may be used to adjust the current (and voltage and gain) in order to arrive at the target brightness for imaging. Thus, as shown in FIG. 6, a delay is present between when the signal to start acquiring images is sent (at time t1) and when the VLI of the first image is used to adjust imaging settings (at time t2). In the example shown, this delay may be 80 ms, but may be longer if the x-ray imaging systems has a longer frame loop time (e.g., the time to acquire an image and determine the VLI of the acquired image).

At time t2, the VLI of the first image is used to adjust the x-ray source current. Because the current is low and ramping toward the final, target current, the VLI of the first image may be low (e.g., 50) relative to a target VLI (e.g., 110). Using a corrected brightness, the VLI of the first image (50) may be corrected by the target current and feedback current, according to equation 3 presented above. For example, if the target current is 3.9 mA and the feedback current is 1.2 mA, the corrected VLI may be $50*\sqrt{3.9/1.2}$, which would be approximately 90. The VLI variation may be −20, resulting in an index skip of 15.

The adjustment of the set current may continue as current ramps toward a target current and as the image brightness ramps toward a target brightness. Around image frame 9, the current begins to stabilize and is fully stabilized by image frame 14.

A technical effect of correcting the video level indicator of an image based on set current and feedback current is the rapid determination of a target x-ray tube voltage and target x-ray tube current, lowering the amount of time needed to stabilize image brightness and reducing patient radiation exposure.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. Are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an x-ray imaging system, comprising:
  acquiring, with the x-ray imaging system, a first image as an x-ray tube current of the x-ray imaging system is ramping to an initial target x-ray tube current;

determining a predicted brightness of a future image to be acquired at the initial target x-ray tube current, the predicted brightness based on a measured brightness of the first image and a feedback x-ray tube current relative to the initial target x-ray tube current;

obtaining a new target x-ray tube current based on the predicted brightness; and commanding the x-ray imaging system to transmit a radiation beam at the new target x-ray tube current;

wherein obtaining the new target x-ray tube current based on the predicted brightness of the first image comprises obtaining the new target x-ray tube current in response to the predicted brightness being outside a threshold range of a target brightness;

wherein obtaining the new target x-ray tube current based on the predicted brightness comprises obtaining an index skip value based on the predicted brightness, adjusting an index value based on the index skip value, and obtaining the new target x-ray tube current according to the adjusted index value; and wherein obtaining the index skip value based on the predicted brightness includes determining a brightness variation based on the predicted brightness and the target brightness and obtaining the index skip value by entering the brightness variation as input to an index skip look-up table that maps index skip values as a function of brightness variation.

2. The method of claim 1, further comprising acquiring, with the x-ray imaging system, one or more additional images, determining a predicted brightness of each additional image, and adjusting the new x-ray tube current based on the predicted brightness of each additional image, until a final additional image having a predicted brightness that is within the threshold range of the target brightness is acquired.

3. The method of claim 2, further comprising responsive to acquiring the final additional image, maintaining x-ray tube current and acquiring a plurality of images at the x-ray tube current.

4. The method of claim 1, wherein determining the predicted brightness includes measuring a video level indicator (VLI) of the first image and correcting the VLI by the feedback x-ray current relative to the initial target x-ray tube current.

5. The method of claim 1, wherein the feedback x-ray tube current comprises an x-ray tube current at which the first image was acquired.

6. A method for an x-ray imaging system, comprising:
acquiring, with the x-ray imaging system, a first image as an x-ray tube current of the x-ray imaging system is ramping to an initial target x-ray tube current;

determining a predicted brightness of a future image to be acquired at the initial target x-ray tube current, the predicted brightness based on a measured brightness of the first image and a feedback x-ray tube current relative to the initial target x-ray tube current obtaining a new target x-ray tube current based on the predicted brightness; and commanding the x-ray imaging system to transmit a radiation beam at the new target x-ray tube current;

wherein obtaining the new target x-ray tube current based on the predicted brightness of the first image comprises obtaining the new target x-ray tube current in response to the predicted brightness being outside a threshold range of a target brightness;

wherein obtaining the new target x-ray tube current based on the predicted brightness comprises obtaining an index skip value based on the predicted brightness, adjusting an index value based on the index skip value, and obtaining the new target x-ray tube current according to the adjusted index value; and wherein obtaining the new target x-ray tube current according to the adjusted index value comprises entering the adjusted index value as input to a current index table that maps x-ray tube current as a function of index value.

7. The method of claim 6, further comprising obtaining a new target x-ray tube voltage by entering the adjusted index value as input to a voltage index table that maps voltage as a function of index value.

* * * * *